(12) United States Patent
Persson

(10) Patent No.: US 6,422,235 B1
(45) Date of Patent: Jul. 23, 2002

(54) VOCAL VALVE WITH FILTER

(75) Inventor: Jan-Ove Persson, Höör (SE)

(73) Assignee: Atos Medical AB, Horby (SE)

( * ) Notice: Subject to any disclaimer, the term of this patent is extended or adjusted under 35 U.S.C. 154(b) by 0 days.

(21) Appl. No.: 09/674,780

(22) PCT Filed: May 12, 1999

(86) PCT No.: PCT/SE99/00803

§ 371 (c)(1),
(2), (4) Date: Dec. 6, 2000

(87) PCT Pub. No.: WO99/60954

PCT Pub. Date: Dec. 2, 1999

(30) Foreign Application Priority Data

May 14, 1998  (SE) .............................................. 9801685

(51) Int. Cl.[7] .............................................. A61M 16/00
(52) U.S. Cl. .............................. 128/200.26; 128/207.16; 623/9
(58) Field of Search ....................... 128/200.26, 207.14, 128/207.16, 912, DIG. 26, 207.29; 623/9

(56) References Cited

U.S. PATENT DOCUMENTS

| | | | | |
|---|---|---|---|---|
| 2,405,851 A | * | 8/1946 | Roberts ........................ 623/9 |
| 2,804,076 A | * | 8/1957 | Giraudon ................ 128/207.16 |
| 3,334,631 A | * | 8/1967 | Stebleton ................ 128/200.26 |
| 4,040,428 A | * | 8/1977 | Clifford .......................... 623/9 |
| 4,044,402 A | * | 8/1977 | Edwards ......................... 623/9 |
| 4,060,856 A | * | 12/1977 | Edwards ......................... 623/9 |
| 4,596,248 A | * | 6/1986 | Lieberman ............. 128/207.16 |
| 4,808,183 A | * | 2/1989 | Panje ..................... 128/207.16 |
| 4,911,716 A | * | 3/1990 | Blom et al. ............ 128/200.26 |
| 5,107,828 A | * | 4/1992 | Koss et al. ............. 128/200.26 |
| 5,259,378 A | * | 11/1993 | Huchon et al. ........ 128/207.16 |
| 5,392,775 A | * | 2/1995 | Adkins, Jr. et al. ............. 623/9 |

* cited by examiner

Primary Examiner—Aaron J. Lewis
(74) Attorney, Agent, or Firm—Merchant & Gould, P.C.

(57) ABSTRACT

A vocal valve for connection to a tracheostoma comprises a filter (16) for moisture and heat exchange at breathing through the vocal valve, and a housing (15) receiving the filter and having a first opening at one side of the filter to be connected to the tracheostoma, and at least one second opening at the opposite side of the filter, which communicates with the surroundings. A manually operated valve element (15') for blocking the air passage through the filter is constructed to close said first opening at manual operation thereof.

12 Claims, 7 Drawing Sheets

VOCAL VALVE WITH FILTER

Figure 1:
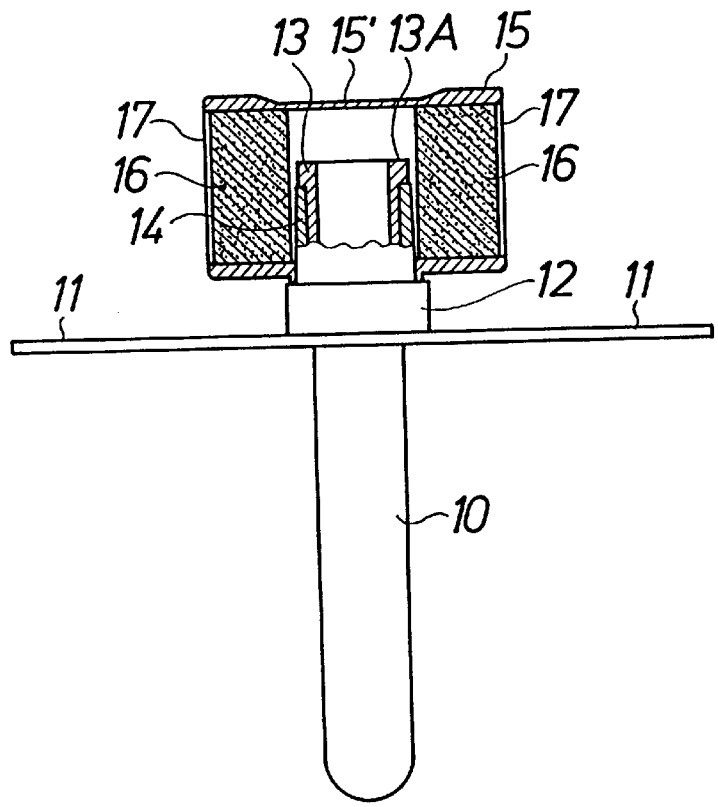

The invention relates to a vocal valve to be applied to a tracheostoma.

A tracheostoma is opened in case a patient has difficulties to breath in a natural way, e.g. due to formation of phlegm, or in case the patient has been laryngeectomized involving excision of the larynx and the vocal cords no connection existing between trachea and the mouth. In the latter case a voice prosthesis often is placed by surgery in a fistula in the wall between trachea and esophagus in order that the patient notwithstanding the lack of vocal cords shall be able to produce speech, which is done by pressing air through the voice prosthesis to esophagus where speech is produced by the mucous membranes being put into vibration. In order that this can take place it is necessary to close the tracheostoma when speech is to be produced, and this is done either by the patient covering the tracheostoma with the fingers or by closing manually a valve located in the tracheostoma. It is necessary to close the tracheostoma also in case the vocal cords are still there because the air otherwise will escape through the tracheostoma instead of escaping via the vocal cords and the mouth in the usual way, but in the latter case the valve can comprise a check valve which opens at inspiration and closes at expiration because the expiration can take place in the normal manner via the vocal cords and the mouth.

For laryngeectomized patients automatic vocal valves have been proposed (U.S. Pat. Nos. 4,582,058 and 4,325,366) which are kept opened during normal breathing but close by a pressure shock being produced in trachea when the patient wishes to produce speech. Valves of this type do not function sufficiently well on patients with a tracheal cannula and therefore are taped directly against the skin of the patient's neck.

On laryngeectomized patients who inspirate and expirate through the tracheostoma, a regenerative moisture and heat exchanger, a so-called "artificial nose", is connected with the tracheostoma. It is formed as a filter which absorbs moisture and heat from the expiration air said moisture and heat hen being given off to the inspiration air (SE-B-348 643 and SE-B-467 195). It has also been proposed according to WO-A-95/17138 to combine such a filter with a valve which can be operated manually in order to close the tracheostoma.

Tracheotomized patients often have some type of cannula, i.e. a curved tube which is passed through the tracheostoma into trachea and the purpose of which is to keep the tracheostoma open and to form a holder for a vocal valve and/or a moisture and heat exchanger which, however, instead can be taped directly against the skin on the patient's neck.

The vocal valve according to the invention is of the kind disclosed in WO-A-95/17138 and comprises a filter for moisture and heat exchange at breathing through the vocal valve, a housing receiving the filter and having a first opening at one side of the filter to be connected to the tracheostoma, at least one second opening at the opposite side of the filter, communicating with the surroundings, and a manually operated valve element for blocking the air passage through the filter.

In the vocal valve according to WO-A-95/17138 the airflow through the tracheostoma via the filter is blocked by closing said second opening at manual operation of the valve element. This involves a clear drawback because only a limited area can be provided in a plane of the opening and thus of the filter in order to effect a sealed closing; otherwise the vocal valve at the necessary filter volume will be unreasonably high. A small area of the filter implies bad moisture and heat exchange.

The purpose of the invention is to overcome this drawback which is achieved by a vocal valve for connection to a tracheostoma, comprising a regenerating filter for moisture and heat exchange at breathing through the vocal valve, a housing receiving the filter and having a first opening at one side of the filter to be connected to the tracheostoma, at least one second opening at the opposite side of the filter, communicating with the surroundings, and a manually operated valve element for blocking the air passage through the filter, characterized that a socket projecting into the interior of the housing forms a valve seat defining said first opening, to be sealaingly engaged by the valve element at manual operation thereof. Thereby, great freedom is achieved with regard to the construction of the filter which can be dimensioned for optimal moisture and heat exchange function, the valve element at the same time having to close a small area only, which requires a very small force at operation of the valve element. If on the contrary the valve element shall close an optimal filter area in the vocal valve according to WO-A-95/17138 a considerably greater force is required, which causes inconvenience for the patient particularly if the vocal valve is provided with a cannula because this passes into a very delicate area of the patient. Above all patients which have recently had surgery are very susceptible.

Figure 2:
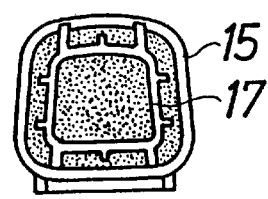
Figure 3:
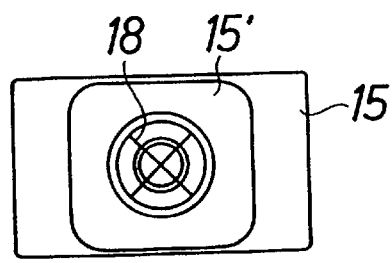
Figure 4:
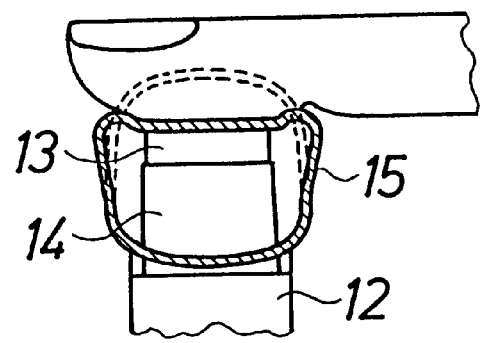
Figure 5:
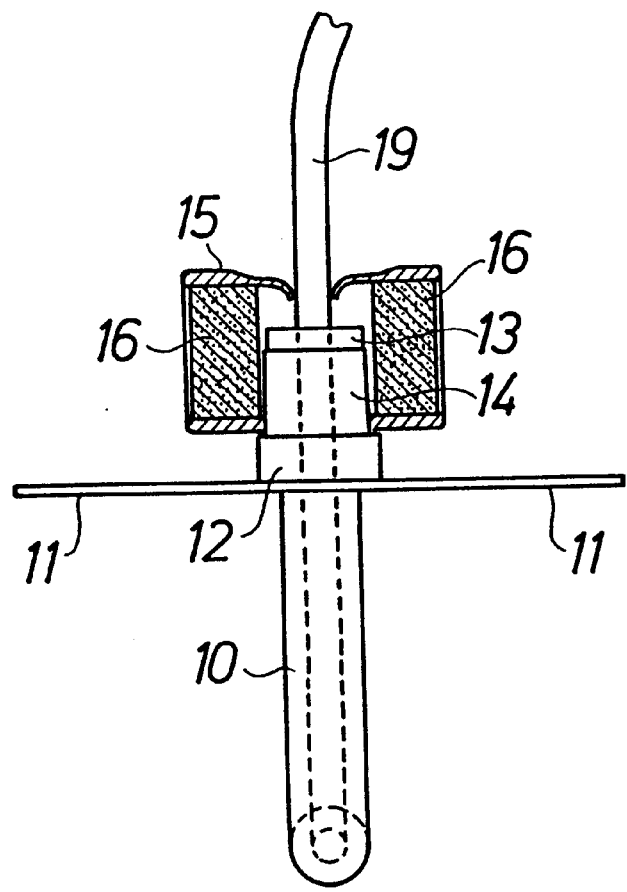
Figure 6:
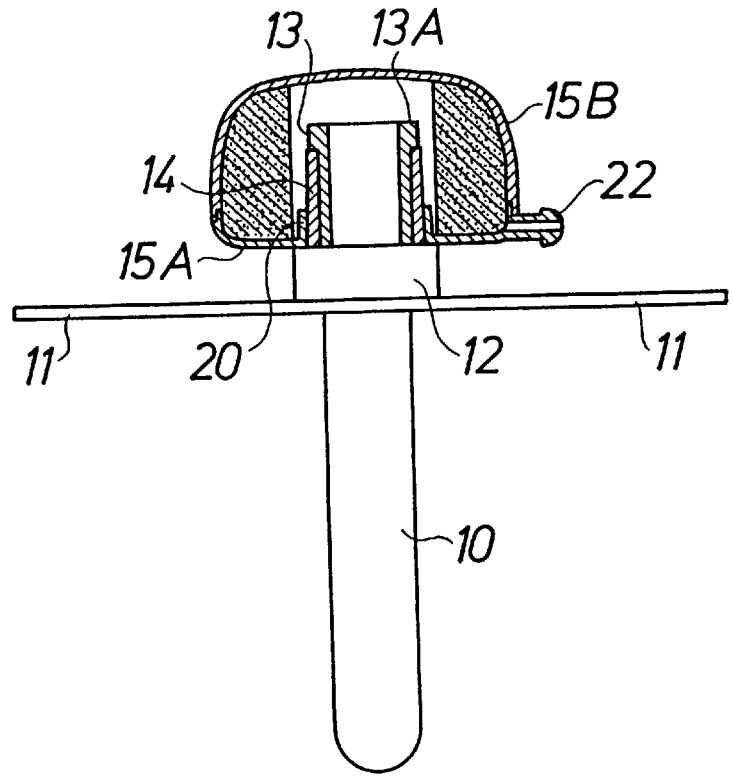
Figure 7:
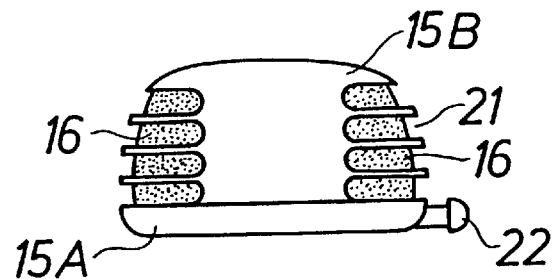
Figure 8:
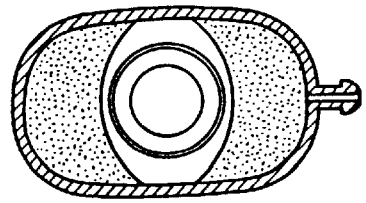
Figure 9:
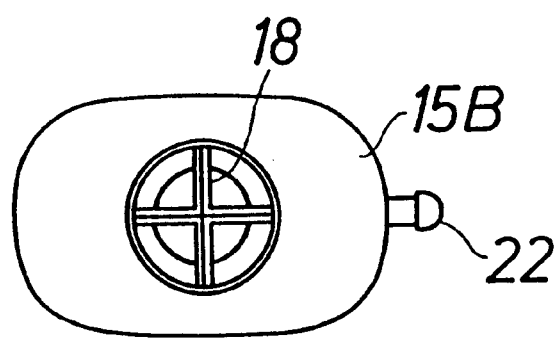
Figure 10:
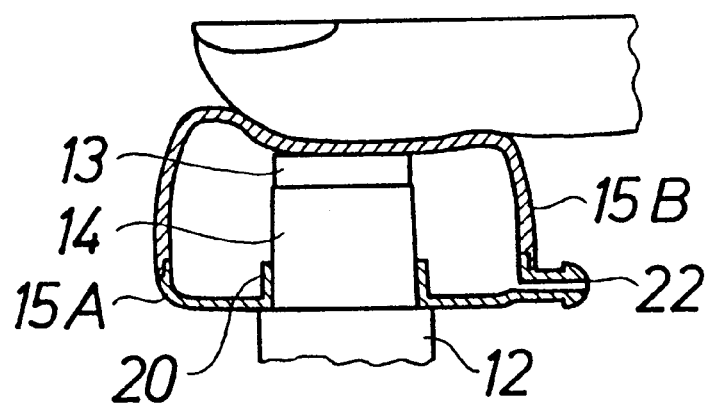
Figure 11:
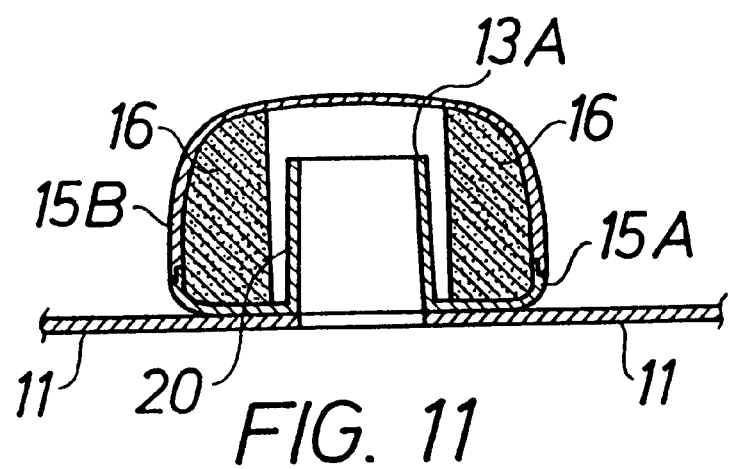
Figure 12:
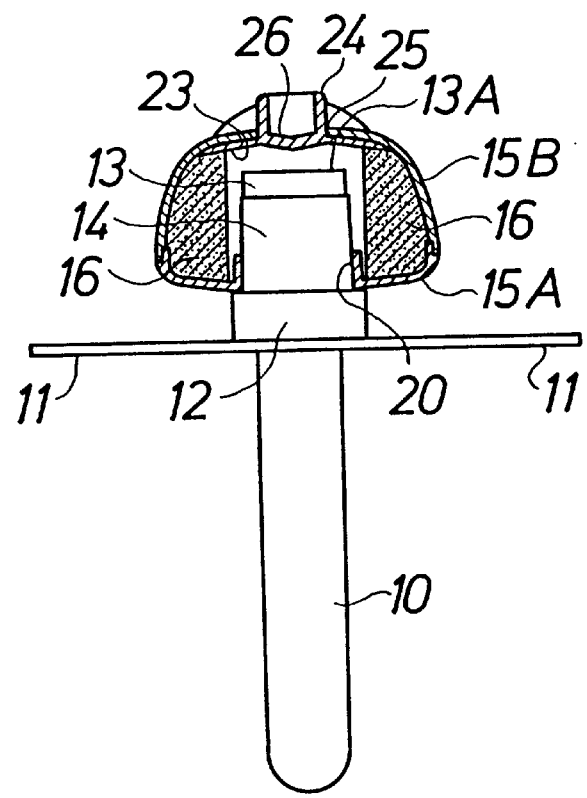
Figure 13:
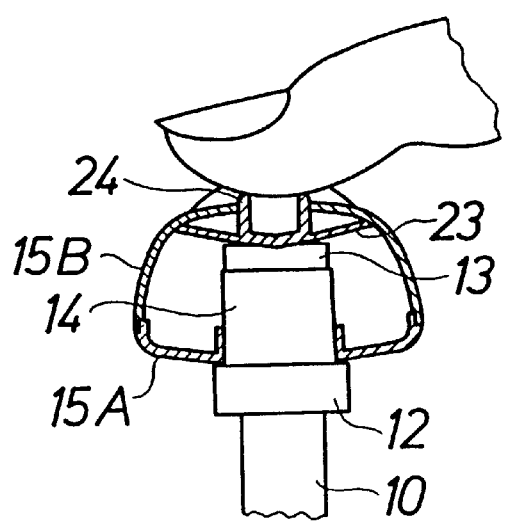
Figure 14:
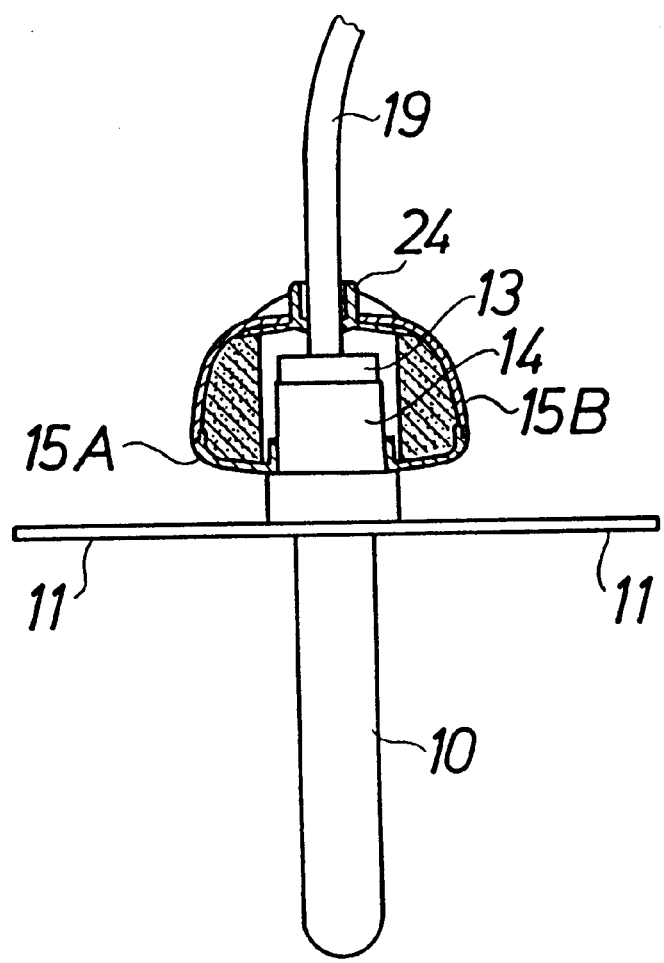
Figure 15:
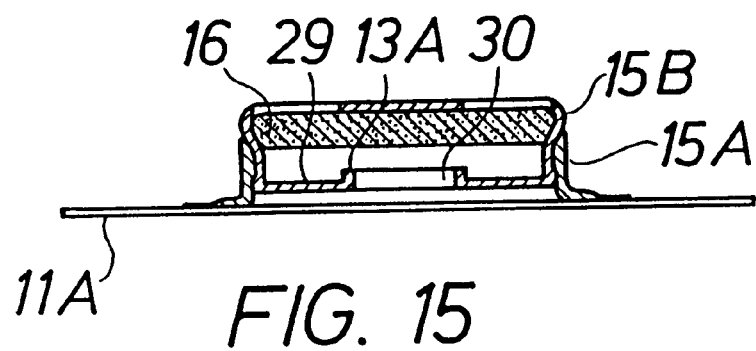
Figure 16:
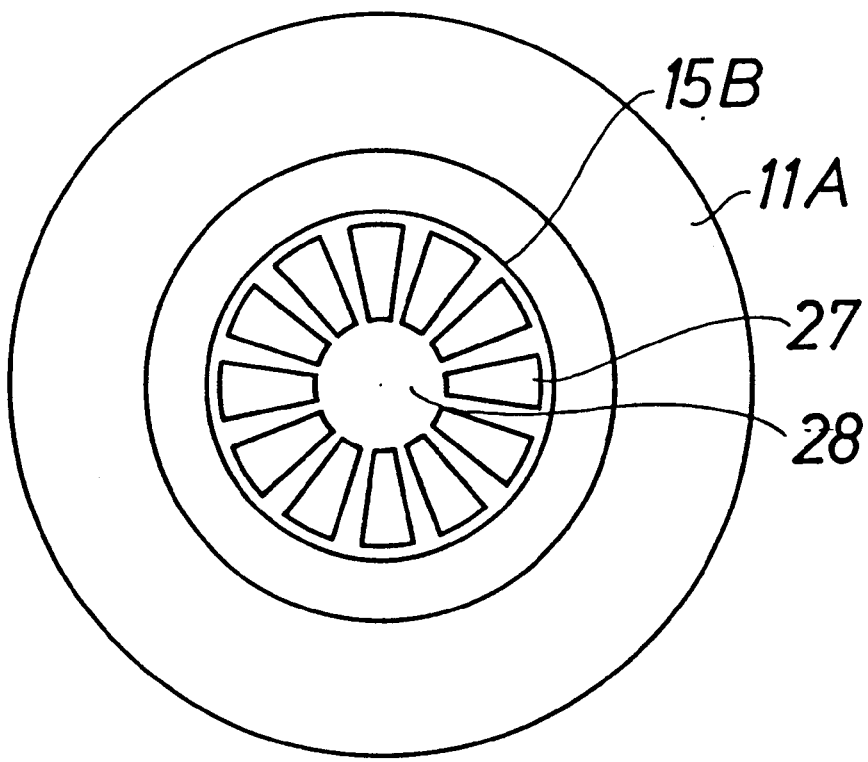
Figure 17:
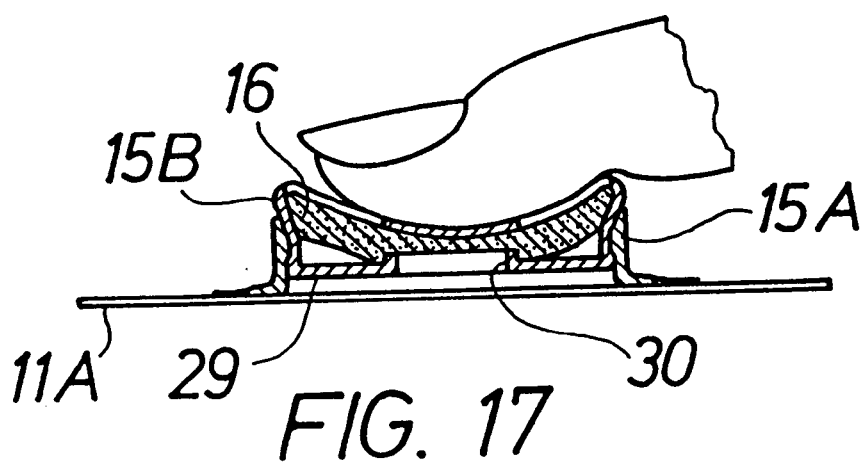

In order to explain the invention in greater detail a number of embodiments will be described below reference being made to the accompanying drawings in which FIG. 1 is a side view, partly in axial cross-section, of a first embodiment of the vocal valve according to the invention, FIG. 2 is an end view of the filter for the regenerative moisture and heat exchanger, FIG. 3 is a plan view of the housing receiving the filter, FIG. 4 is a cross-sectional view of the housing receiving the filter, and illustrates the manual operation for blocking the air passage through the filter, FIG. 5 is a view corresponding to FIG. 1 with a suction catheter passed through the vocal valve, FIG. 6 is a view similar to FIG. 1 of a second embodiment of the vocal valve according to the invention, FIG. 7 is a side view of the housing receiving the filter, FIG. 8 is a cross-sectional view of the filter and the housing receiving the filter, FIG. 9 is a plan view of the housing, FIG. 10 is a view similar to FIG. 4, which illustrates the manual operation for blocking the air passage through the filter, FIG. 11 is a view similar to FIG. 6 of a modification of the vocal valve in FIGS. 6–9, FIG. 12 is a view similar to FIG. 1 of a third embodiment of the vocal valve according to the invention, FIG. 13 is a view similar to FIGS. 4 and 10 of the embodiment in FIG. 12, FIG. 14 is a view similar to FIG. 5 of the embodiment in FIG. 12, FIG. 15 is an axial cross-sectional view of a fourth embodiment of the invention, FIG. 16 is a plan view of the embodiment in FIG. 15, and FIG. 17 is a view similar to FIG. 4 and illustrates manual operation of the vocal valve according to FIGS. 15 and 16.

Referring to FIGS. 1–3 the embodiment of the vocal valve according to the invention shown therein comprises a curved tracheal cannula 10 to be inserted into a tracheostoma and provided with two flexible wings or flaps 11 which are fixed against the skin of the neck by means of a strap passed around the neck and attached to the flaps. The flaps 11 are attached to the lower side of a flange 12 on the tracheal cannula, and a bushing 14 consisting of an ISO-cone for connection to a respirator or another apparatus is provided between the flange 12 and an end flange 13 provided on the tracheal cannula, which forms the seat surface 13a of the vocal valve. A housing 15 is mounted on the bushing 14 and comprises a socket of relatively soft plastics open at both ends. In cross-section the housing has substantially rectangular shape with rounded corners as can be seen from FIG. 2. Inside the housing two filter bodies 16 are provided which are retained therein between an end grid 17 and the part of the tracheal cannula 10 which projects into the housing. The filter bodies can consist of a foam material e.g. foamed polyurethane impregnated with calcium chloride.

At breathing through the vocal valve the expiration air passes through the tracheal cannula 10 and enters the housing 15 through the opening surrounded by the seat 13A in order then to pass through the filter bodies 16 to the surrounding air, while the inspiration air passes in the opposite direction into the tracheal cannula 10. The filter bodies form a regenerative moisture and heat exchanger, heat and moisture being absorbed by the filter from the expiration air in order then to be given off to the inspiration air.

When speech is to be produced the passage of air through the vocal valve shall be blocked in order that the expiration air shall be expelled through the mouth via the vocal cords or—for a laryngeectomized patient—via a voice prosthesis in the wall between trachea and esophagus, and this is effected according to FIG. 4 by deforming the housing 15 with a finger and sealingly engage the housing with the seat surface 13A. In order to facilitate the deformation of the valve housing 15 a portion 15' thereof, centered over the seat surface 13A, is made with a smaller wall thickness than the rest of the valve housing. In this portion of the valve housing weakening lines 18 are provided as an impervious cross, and by pressing a blunt object e.g. a pencil against the centre of this cross the wall of the filter housing can be penetrated, four pointed flaps being established so that an opening is provided in the housing wall through which a suction catheter 19, FIG. 5, can be introduced into trachea through the tracheal cannula 10 for sucking away phlegm from trachea in patients having a large phlegm production and difficulties to cough off such phlegm. When the material of the valve housing 15 is relatively soft the flaps will retain their original position after withdrawal of the suction catheter so that the opening in the housing wall will again be substantially closed. Since only a minor number of patients need phlegm suction this embodiment is advantageous. The alternative would be that the vocal valve has to be supplied in two versions one with a suction port and one without, because patients which need no phlegm suction do not want to have an open suction port in the vocal valve.

In the embodiment of the vocal valve according to the invention which is disclosed in FIGS. 6–9 the valve housing is made of two parts 15A and 15B the part 15A forming a bottom plate which at an upwardly projecting collar 20 is passed onto the ISO-cone 14. The part 15B forms a cover on the bottom plate 15A and is connected with the bottom plate in order to enclose the filter bodies 16. The cover 15B has a number of openings 21 in order to communicate the interior of the valve housing with the surrounding air via the filter bodies 16.

In order to block the air passage through the vocal valve the cover 15B can be deformed with a finger in order to sealingly engage the cover with the valve seat 13A as shown in FIG. 10 and described above. In this case the bottom plate 15A is provided with a nipple 22 for connection of an oxygen hose. This nipple can consist of a fixedly arranged nipple or, alternatively, can consist of a separate nipple which is inserted into a connection aperture in the valve housing.

In the same manner as described above a suction catheter can be passed through an aperture in the valve housing said aperture being opened by penetrating an impervious cross 18 on the cover 15B in the same manner as disclosed in FIG. 5.

A modification of the embodiment in FIGS. 6–9 is disclosed in FIG. 11 the tracheal cannula 10 being omitted in this modification and the flaps 11 being attached directly to the lower side of the bottom plate 15A. In this embodiment the collar 20 is extended upwards to form the seat surface 13A. The passage formed by the collar 20 communicates directly with the tracheostoma when the vocal valve is attached to the patient by the flaps 11 being taped against the skin of the patient's neck.

Instead of being made of a soft material the valve housing 15 can be made of a rigid material and a separate valve element can be provided inside the valve housing for co-operation with the valve seat 13A, said valve element being operated from the outside of the valve housing. For example, the valve element can have a valve stem projecting through an aperture in the valve housing in the portion 15'. Such an embodiment is disclosed in FIGS. 12 and 13. A valve disc 23 is connected to the cover 15B at the inside thereof and has a socket 24 projecting through an aperture 25 in the cover. Normally the valve disc 23 and the socket 24 are in this position which is shown in FIG. 12 but can be operated manually from the outside by means of a finger to engage sealingly the valve disc under elastic deformation with the seat surface 13A as shown in FIG. 13. A cross of impervious weakening lines can be provided in the bottom wall 26 of the socket 24 in the manner described above in order to allow a suction catheter to be passed through the valve housing into and through the tracheal cannula as disclosed in FIG. 14.

In the embodiment according to FIGS. 16 and 17 the valve housing comprises a bottom part 15A and a cover part 15B, the bottom part 15A being attached to a flexible flange 11A and the cover part 15B being connected with the bottom part 15A. Inside the cover part 15B a filter body 16 is provided, and this part is made with a number of apertures 27 around an impervious central portion 28 in order to communicate the interior of the valve housing with the surroundings via the filter body 16 which covers the apertures 27. A plate 29 inside the cover part 15B has a central ring 30 through which the interior of the valve housing communicates with the tracheostoma when the vocal valve is attached to the patient by the flange 11A being taped against the skin of the patient's neck with the ring 30 centred on the tracheostoma. When the patient with a finger presses on the impervious central portion 28 of the cover part 15B said part will be deformed and also the filter body 16 which will be sealingly engaged with and compressed against the seat surface 13A formed by the ring 30, as shown in FIG. 17, in order to block the air passage through the vocal valve.

In this embodiment the cover part 15B with the filter body 16A can comprise a replaceable filter unit, the bottom part 15A being intended to be used permanently for application of the replaceable filter unit over the tracheostoma.

In all the embodiments of the vocal valve according to the invention, which have been described, the opening communicating with the tracheostoma is closed in order to block the air flow through the vocal valve the regenerating moisture and heat exchanging filter as a consequence thereof can be dimensioned for optimal function without the vocal valve projecting unacceptably far from the tracheostoma. In case the vocal valve is combined with a tracheal cannula the optimally dimensioned filter can be located inwardly of the cannula end (the seat surface 13A).

The vocal valve according to the invention involves a low manufacturing cost, particularly in case the wall of the valve housing is deformed in order to close the vocal valve and to block the air flow therethrough, because the vocal valve in this embodiment has no moving parts.

What is claimed is:

1. Vocal valve for connection to a tracheostoma, the valve comprising:

a regenerating filter for moisture and heat exchange at breathing through the vocal valve;

a housing receiving said filter therein, said housing defining a first opening at a first side of said filter, said first opening being adapted to be connected to the tracheostoma, and at least one second opening at a second side of said filter, said second opening being in communication with an environ surrounding said housing;

a manually operable valve element; and a projecting socket disposed within said housing comprising a valve seat around said first opening;

wherein when said valve element is operated, said valve element and said valve seat cooperate to block passage of air through said first opening.

2. Vocal valve according to claim 1, wherein said valve comprises a tracheal cannula, said first opening being defined at an end thereof.

3. Vocal valve according to claim 1, further comprising a sealing surface around said first opening formed by the housing.

4. Vocal valve according to claim 3, wherein said sealing surface comprises an end surface of said projecting socket.

5. Vocal valve according to claim 1, wherein said manually operable valve element comprises a wall portion of said housing, said wall portion being resiliently deformable so as to sealingly engage with said valve seat to block passage of air through said first opening.

6. Vocal valve according to claim 1, wherein said filter is disposed between a wall portion of said housing and said first opening, said manually operable valve element comprising said wall portion, said wall portion being resiliently deformable so as to press said filter against said first opening, so as to block passage of air said first opening and said filter.

7. Vocal valve according to claim 5, wherein the housing (15) comprises relatively soft material.

8. Vocal valve according to claim 5, wherein a wall thickness of said resiliently deformable wall portion of said housing is less than a wall thickness of said housing other than at said wall portion.

9. Vocal valve according to claim 1, wherein said valve comprises two filter bodies, and said socket is open at each end thereof, said first opening being defined between said two filter bodies.

10. Vocal valve according to claim 1, wherein said manually operable valve element comprises a valve disk disposed inside said housing and an operating member disposed outside said housing.

11. Vocal valve according to claim 1, wherein said valve disc comprises a resiliently deformable plate connected to said housing.

12. Vocal valve according to claim 1, wherein said housing defines impervious weakening lines such that said housing is penetrable to receive a suction catheter.

* * * * *